United States Patent
Parry et al.

(10) Patent No.: US 6,968,233 B1
(45) Date of Patent: Nov. 22, 2005

(54) IMPLANTABLE CARDIAC STIMULATION DEVICE INCLUDING A SYSTEM FOR AND METHOD OF AUTOMATICALLY INDUCING A TACHYARRHYTHMIA

(75) Inventors: John Thomas Parry, Novi, MI (US); Gary Robert Viviano, Brighton, MI (US); James Edward Gantz, Jr., Cincinnati, OH (US)

(73) Assignee: Pacesetter, Inc., Sylmar, CA (US)

( * ) Notice: Subject to any disclaimer, the term of this patent is extended or adjusted under 35 U.S.C. 154(b) by 627 days.

(21) Appl. No.: 10/177,425

(22) Filed: Jun. 20, 2002

Related U.S. Application Data

(63) Continuation-in-part of application No. 09/552,299, filed on Apr. 18, 2000, now Pat. No. 6,453,197.

(51) Int. Cl.$^7$ ............................................. A61N 1/362
(52) U.S. Cl. ........................ 607/28; 607/9; 607/14; 607/27
(58) Field of Search ........................... 607/4–9, 14–15, 607/27–28, 11, 17; 600/509, 515, 518–519

(56) References Cited

U.S. PATENT DOCUMENTS

| | | | | |
|---|---|---|---|---|
| 4,390,021 A | * | 6/1983 | Spurrell et al. ............. | 128/419 |
| 4,686,988 A | | 8/1987 | Sholder ................. | 128/419 PT |
| 4,708,142 A | | 11/1987 | DeCote, Jr. ........... | 128/419 PT |
| 4,712,555 A | | 12/1987 | Thornander et al. .. | 128/419 PG |
| 4,729,376 A | | 3/1988 | DeCote, Jr. ........... | 128/419 PT |
| 4,788,980 A | | 12/1988 | Mann et al. .......... | 128/419 PG |
| 4,870,974 A | * | 10/1989 | Wang ......................... | 600/513 |
| 4,940,052 A | | 7/1990 | Mann et al. .......... | 128/419 PG |
| 4,944,298 A | | 7/1990 | Sholder ................ | 128/419 PG |
| 4,969,467 A | | 11/1990 | Callaghan et al. .... | 128/419 PG |
| 5,312,449 A | * | 5/1994 | Nigam ........................ | 607/14 |
| 5,350,410 A | | 9/1994 | Kleks et al. .................. | 607/28 |
| 5,653,740 A | | 8/1997 | Degroot et al. ............... | 607/92 |
| 5,709,711 A | | 1/1998 | Fain ............................. | 607/8 |
| 5,899,929 A | * | 5/1999 | Thompson et al. ........... | 607/28 |
| 5,925,067 A | * | 7/1999 | Lu ............................... | 607/28 |
| RE36,765 E | | 7/2000 | Mehra .......................... | 607/4 |
| 6,675,042 B2 | | 1/2004 | Swerdlow et al. ............ | 607/8 |

* cited by examiner

Primary Examiner—Kennedy Schaetzle
Assistant Examiner—John D Alexander

(57) ABSTRACT

A system and method for use in an implantable cardiac stimulation device permits automatic induction of a tachyarrhythmia of a heart to permit the performance of an electrophysiological test of the heart. A pulse generator repeatedly delivers a group of first and second sets of pacing pulses to a chamber of the heart. The pacing pulses are separated in time by interpulse intervals to overdrive pace a chamber of the heart. A processor, coupled to the pulse generator, varies the second set of interpulse intervals according to a predetermined protocol after each group of pacing pulses is delivered to the chamber of the heart. The successive groups of pacing pulses are delivered to the heart until the tachyarrhythmia is induced.

32 Claims, 4 Drawing Sheets

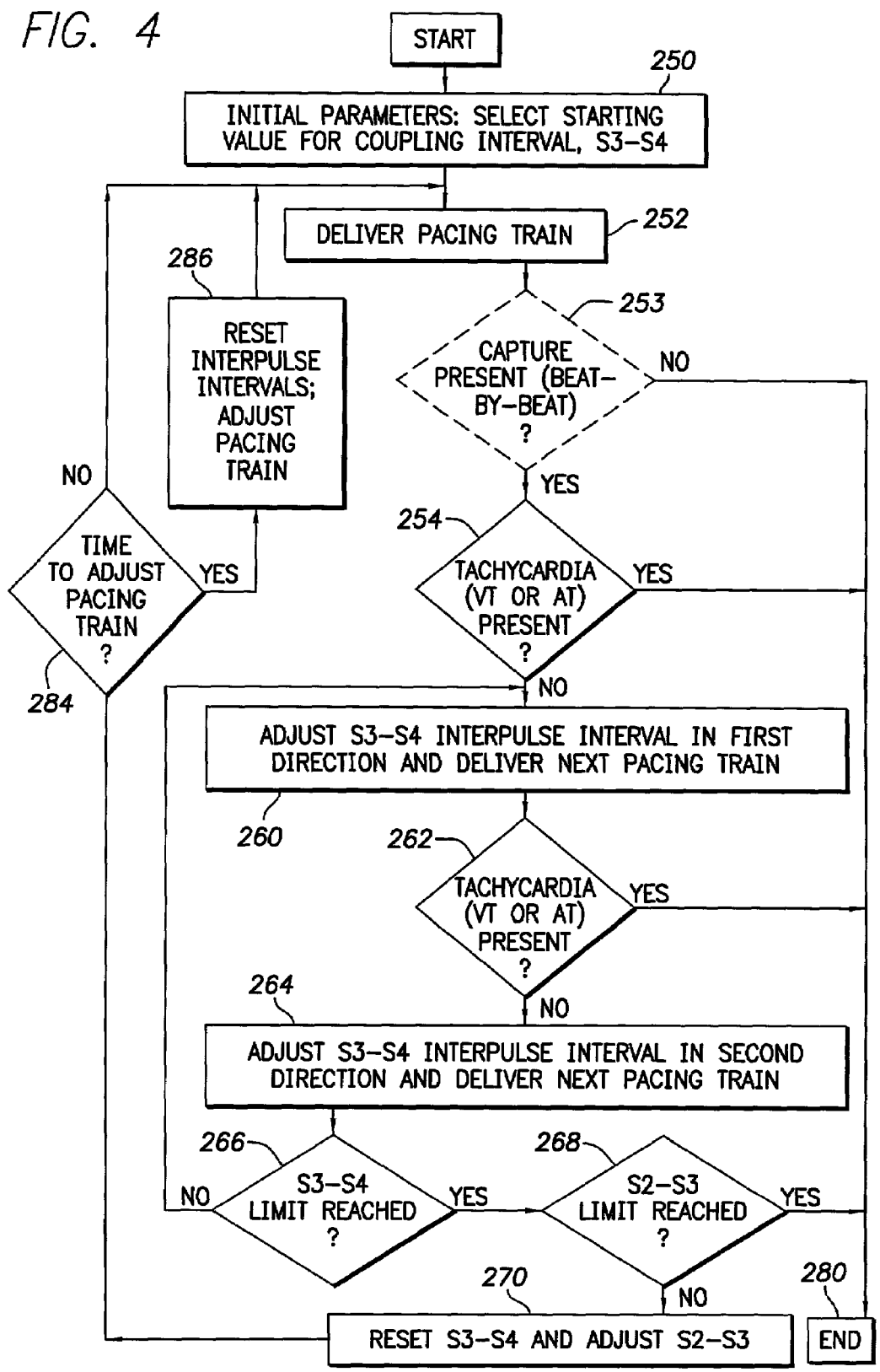

IMPLANTABLE CARDIAC STIMULATION DEVICE INCLUDING A SYSTEM FOR AND METHOD OF AUTOMATICALLY INDUCING A TACHYARRHYTHMIA

CROSS-REFERENCE TO RELATED APPLICATIONS

This application is a continuation-in-part of U.S. patent application Ser. No. 09/552,299, filed Apr. 18, 2000, titled "Implantable Cardiac Stimulation Device Including a System For and Method of Automatically Inducing a Tachyarrhythmia," now U.S. Pat. No. 6,453,197.

FIELD OF THE INVENTION

The present invention generally relates to an implantable cardiac stimulation device. The present invention more particularly relates to such a device which includes a system for and implements a method of automatically conducting a non-invasive programmed stimulation (NIPS) procedure for inducing a tachyarrhythmia of a heart to permit the performance of electrophysiological studies.

BACKGROUND OF THE INVENTION

Frequently, a clinician must perform electrophysiological studies in patients having implanted permanent pacemakers or cardioverters/defibrillators to determine accurately the patient's pathological condition, cardiovascular characteristics and other information needed in order to prescribe a particular therapeutic treatment for the patient. Such studies often require the inducement of a tachyarrhythmia of the heart such as ventricular tachycardia.

Originally, these studies were invasive because they required the surgical insertion of instruments such as temporary intracardiac pacing catheters into the patient. Thus, these studies were accompanied by some risk and preferably were performed in hospitals. Therefore, these studies were not only expensive, but also time consuming and caused patient anxiety.

In order to avoid medical risks to the patient and hospitalization, non-invasive programmed stimulation (NIPS) procedures have been developed to permit the electrophysiological studies to be performed in a physician's office during routine follow-up visits.

These procedures utilize the implanted cardiac stimulation device and an external programmer. By virtue of the presence of a permanent pacing/defibrillation lead associated with the implanted cardiac stimulation device, the need for placement of a temporary intracardiac pacing catheter is eliminated. Typically, NIPS procedures consist generally of the application of premature electrical pulses at precise intervals to the myocardium of the patient's heart by the implanted cardiac stimulation device and its associated lead or leads. The implanted device applies the stimulation pulses under commands from the external programmer which is manually controlled by the clinician. Prior to the procedure, the clinician manually defines the intervals between the successive stimulation pulses on the programmer. After the implanted device applies the succession of stimulation pulses to the heart, the clinician then, on the programmer, manually observes results such as tachyarrhythmia induction or lack of capture by the stimulation pulses. Thereafter, the clinician alters the stimulation pulse intervals and causes the programmer to initiate another application of the successive stimulation pulses to the patient's heart by the implanted cardiac stimulation device. As a result, NIPS studies, as currently constituted, are tedious to administer, consume considerable time, and lead to considerable cost to the electrophysiology laboratory.

SUMMARY OF THE INVENTION

The present invention provides a system and method for use in an implantable cardiac stimulation device that automatically induces a tachyarrhythmia of a heart to permit the performance of an electrophysiological test of the heart. In accordance with the present invention, the system and method permits the implantable cardiac stimulation device to perform a NIPS procedure automatically once initial parameters are established in the device by an external programmer under control of a clinician.

In accordance with the present invention, a NIPS protocol is stored in a memory within the implantable cardiac stimulation device. A processor accesses the NIPS protocol stored in the memory to control a pulse generator that repeatedly delivers groups of pacing pulses to a chamber of the heart. The pacing pulses are separated in time by pacing or interpulse intervals to overdrive pace the patient's heart. After each group of pacing pulses is delivered to the heart, the processor varies the pacing intervals according to the NIPS protocol prior to reinitiating the delivery of the next group of stimulation pulses. The processor terminates the delivery of the stimulation pulses if it detects the tachyarrhythmia of the heart after a group of stimulation pulses have been delivered to the heart.

In accordance with a further aspect of the present invention, the processor, in accordance with the NIPS protocol, determines capture of the heart by each delivered stimulation pulse and terminates the delivery of the stimulation pulses to the heart by the pulse generator when a predetermined number of successive pacing pulses fail to capture the heart. In accordance with a still further aspect of the present invention, the processor requires a minimum pacing interval to determine capture of the heart by a stimulation pulse. In accordance with the NIPS protocol, the processor terminates the delivery of the stimulation pulses to the heart when a pacing interval falls below the minimum pacing interval.

In accordance with still further aspects of the present invention, each group of stimulation pulses includes a first set of pulses employed to capture the heart at an overdrive pacing rate and a second set of pulses to induce the tachyarrhythmia. The processor, in accordance with the NIPS protocol, varies the pacing intervals of the second set of pacing pulses between the application of the groups of stimulation pulses.

In accordance with still further particular aspects of the present invention, the second set of pacing pulses includes a last pulse and a second to the last pulse and the processor decrements the pacing interval between the last pulse and the second to the last pulse responsive to the last pulse capturing the heart in accordance with the NIPS protocol. Further, the second set of pacing pulses further includes a third to the last pulse. The processor, in accordance with the NIPS protocol, decrements the pacing interval between the second to the last pulse and the third to the last pulse and resets the pacing interval between the last pulse and the second to the last pulse to an initial interval responsive to the last pulse failing to capture the heart.

In another embodiment, the process may utilize any starting value for the interpulse interval for the inducing pulses.

In another embodiment, the process may be adjusted in any direction and will likely be selected based on the starting interpulse interval value.

In another embodiment, the interpulse interval for the overdrive pulses in the pulse train may be varied after a predetermined time or number of unsuccessful attempts.

In another embodiment, the determination of the presence of a tachycardia may be either a ventricular tachycardia or an atrial tachycardia.

The application of the successive groups of pacing pulses is automatically continued with intergroup pacing interval adjustment until the tachyarrhythmia is detected by the processor. The procedure may further be terminated when manually terminated by the clinician, when a predetermined number of pacing pulses fail to capture the heart, or when a pacing interval falls below the minimum interval required by the processor to determine capture of the heart.

BRIEF DESCRIPTION OF THE DRAWINGS

Further features and advantages of the present invention may be readily understood by reference to the following description taken in conjunction with the accompanying drawings, in which:

FIG. 4 shows a flow chart describing an overview of the operation of the device of FIG. 1 in accordance with an alternative embodiment of the present invention.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
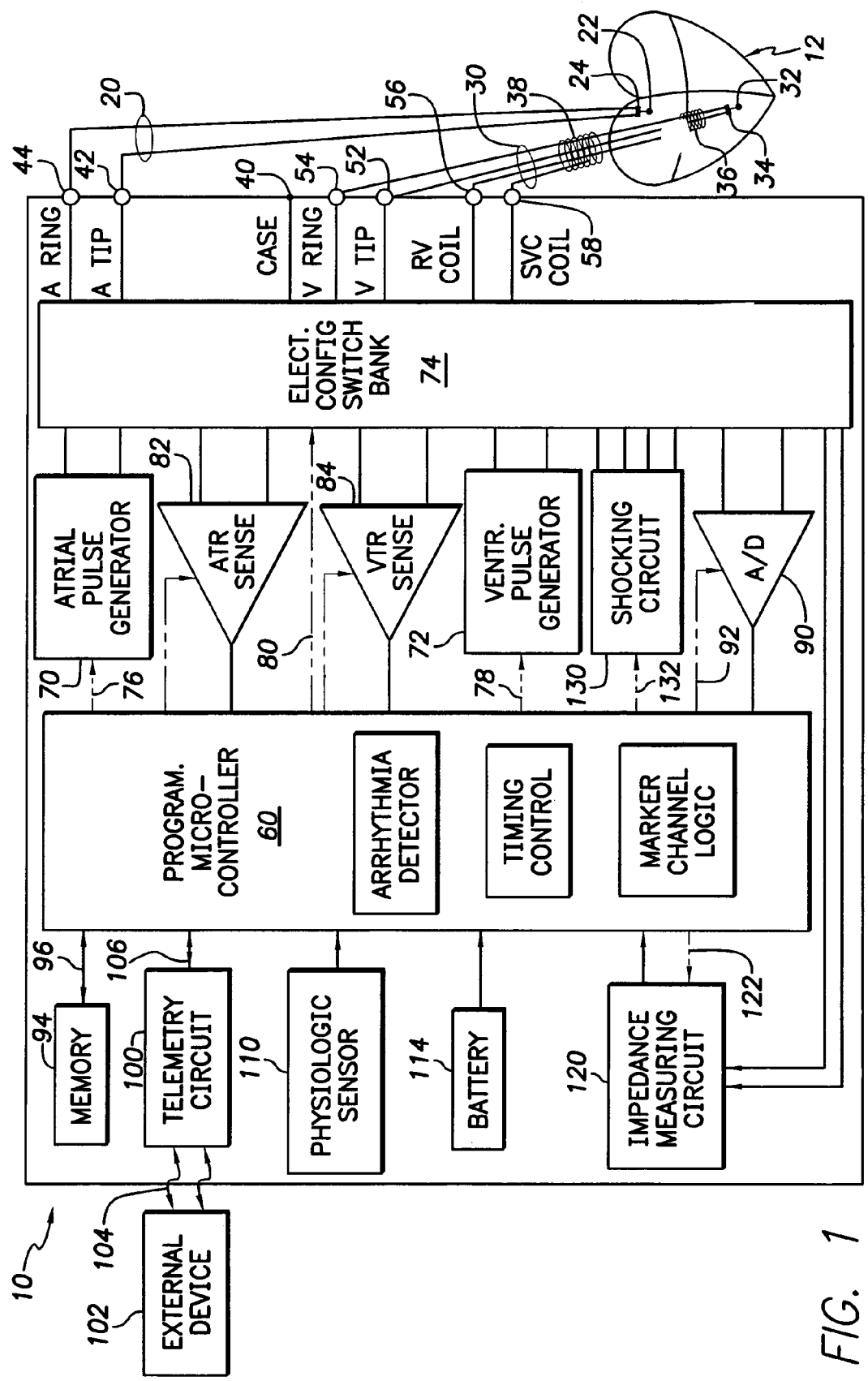
FIG. 1 is a functional block diagram of a dual-chamber implanted stimulation device illustrating the basic elements of a stimulation device which can provide cardioversion, defibrillation, and pacing stimulation, which device embodies and may utilize the present invention to advantage.

In FIG. 1, a simplified block diagram is shown of a dual-chamber implantable stimulation device 10 embodying the present invention and which is capable of treating both fast and slow arrhythmias with stimulation therapy, including cardioversion, defibrillation, and pacing stimulation. While a dual-chamber device is shown, this is for illustration purposes only, and one of skill in the art could readily eliminate or disable the appropriate circuitry to provide a single-chamber stimulation device capable of treating one chamber with cardioversion, defibrillation and pacing stimulation.

To provide atrial chamber pacing stimulation and sensing, the stimulation device 10 is shown in electrical communication with a patient's heart 12 by way of an implantable atrial lead 20 having an atrial tip electrode 22 and an atrial ring electrode 24 which typically is implanted in the patient's atrial appendage.

The stimulation device 10 is also shown in electrical communication with the patient's heart 12 by way of an implantable ventricular lead 30 having, in this embodiment, a ventricular tip electrode 32, a ventricular ring electrode 34, a right ventricular (RV) coil electrode 36, and an SVC coil electrode 38. Typically, the ventricular lead 30 is transvenously inserted into the heart 12 so as to place the RV coil electrode 36 in the right ventricular apex, and the SVC coil electrode 38 in the superior vena cava. Accordingly, the ventricular lead 30 is capable of receiving cardiac signals, and delivering stimulation in the form of pacing and shock therapy to the right ventricle.

While only two leads are shown in FIG. 1, it is to be understood that additional stimulation leads (with one or more pacing, sensing and/or shocking electrodes) may be used in order to efficiently and effectively provide pacing stimulation to the left side of the heart or atrial cardioversion and/or defibrillation. For example, a lead designed for placement in the coronary sinus region could be implanted to deliver left atrial pacing, atrial shocking therapy, and/or for left ventricular pacing stimulation.

The housing 40 (shown schematically) for the stimulation device 10 includes a connector (not shown) having an atrial tip terminal 42 and an atrial ring terminal 44, which are adapted for connection to the atrial tip electrode 22 and the atrial ring electrode 24, respectively. The housing 40 further includes a ventricular tip terminal 52, a ventricular ring terminal 54, a ventricular shocking terminal 56, and an SVC shocking terminal 58, which are adapted for connection to the ventricular tip electrode 32, the ventricular ring electrode 34, the RV coil electrode 36, and the SVC coil electrode 38, respectively. The housing 40 (often referred to as the "can", "case" or "case electrode") may be programmably selected to act as the return electrode, or anode, alone or in combination with one of the coil electrodes, 36 and 38. For convenience, the names of the electrodes are shown next to the terminals.

The stimulation device 10 further includes a programmable microcontroller 60 which controls the various modes of stimulation therapy including a non-invasive programmed stimulation (NIPS) procedure in accordance with the present invention. As is well known in the art, the microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art. Representative types of control circuitry that may be used for embodying the invention include the microprocessor-based control system of U.S. Pat. No. 4,940,052 (Mann et al.), the state-machine of U.S. Pat. No. 4,712,555 (Sholder) and U.S. Pat. No. 4,944,298 (Sholder). For a more detailed description of the various timing intervals used within the stimulation device and their interrelationship, see U.S. Pat. No. 4,788,980 (Mann et al.). The '052, '555, '298 and '980 patents are incorporated herein by reference. As shown in FIG. 1, an atrial pulse generator 70 and a ventricular pulse generator 72 generate pacing stimulation pulses for delivery by the atrial lead 20 and the ventricular lead 30, respectively, via a switch bank 74. The pulse generators, 70 and 72, are controlled by the microcontroller 60 via appropriate control signals, 76 and 78, respectively, to trigger or inhibit the stimulation pulses. The microcontroller 60 further includes timing circuitry that controls the operation of the stimulation device timing of such stimulation pulses (e.g., pacing rate and atrio-ventricular (AV) delay), as well as keeping track of the timing of any refractory periods, PVARP intervals, noise detection windows, evoked response windows, alert intervals, marker channel timing, etc., that is well known in the art.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar or bipolar) by selectively closing the appropriate combination of switches (not shown) as is known in the art. An atrial sense amplifier 82 and a ventricular sense amplifier 84 are also coupled to the atrial and ventricular leads 20 and 30, respectively, through the switch bank 74 for detecting the presence of cardiac activity. The switch bank 74 determines the "sensing polarity" of the cardiac signal by selectively closing the appropriate switches, as is also known in the art. In this way, the clinician may program the sensing polarity independent of the stimulation polarity.

Each sense amplifier, 82 and 84, preferably employs a low power, precision amplifier with programmable gain and/or automatic gain control, bandpass filtering, and a threshold detection circuit, known in the art, to selectively sense the cardiac signal of interest. The automatic gain control enables the device 10 to deal effectively with the difficult problem of sensing the low frequency, low amplitude signal characteristics of ventricular fibrillation.

The outputs of the atrial and ventricular sense amplifiers, 82 and 84, are connected to the microcontroller 60 which, in turn, inhibit the atrial and ventricular pulse generators, 70 and 72, respectively, in a demand fashion whenever cardiac activity is sensed in the respective chambers.

For arrhythmia detection, the device 10 utilizes the atrial and ventricular sense amplifiers, 82 and 84, to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between sensed events (e.g., the P—P and R—R intervals) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, also known as "tiered therapy"). In accordance with the present invention, the microcontroller 60 may employ a high rate classification to determine if a tachyarrhythmia is present for terminating the NIPS procedure when the tachyarrhythmia has been induced by the NIPS procedure.

Cardiac signals are also applied to the inputs of an analog to digital (A/D) data acquisition system 90. The data acquisition system 90 is configured to sense or acquire intracardiac electrogram signals, convert the raw analog data into a digital signal, and store the digital signals for later processing and/or telemetric transmission to an external device 102.

The data acquisition system 90 is coupled to the atrial and ventricular leads, 20 and 30, through the switch bank 74 to sample cardiac signals across any pair of desired electrodes.

The data acquisition system is preferably coupled to the microcontroller, or other detection circuitry, for detecting an evoked response from the heart 12 in response to an applied stimulus, thereby aiding in the detection of "capture". As will be seen hereinafter, capture detection is especially desirable in implementing a NIPS procedure. Capture occurs when an electrical stimulus applied to the heart is of sufficient energy and applied at an appropriate time in a cardiac cycle to depolarize the cardiac tissue, thereby causing the heart muscle to contract. The microcontroller 60 detects a depolarization signal during a window following a stimulation pulse, the presence of which indicates that capture has occurred. The microcontroller 60 may enable capture detection by starting a capture detection window when a ventricular stimulation pulse is issued using the timing circuitry within the microcontroller 60, and enabling the data acquisition system 90 via control signal 92 to sample the cardiac signal that falls in the capture detection window and, based on the amplitude, determines if capture has occurred. As is known in the art, this form of capture detection requires a minimum interpulse interval to sustain the window detection. Further, capture detection is preferably performed on a beat-by-beat basis during a NIPS procedure.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Mann et al.), which patents are hereby incorporated herein by reference. The type of capture detection system used is not critical in the implementation of the present invention.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 28 within each respective tier of therapy. The memory 94 preferably also stores a NIPS protocol from which the microcontroller automatically controls the NIPS procedure.

The operating parameters of the implantable device 10, the NIPS protocol, and the NIPS initializing parameters or values may be non-invasively programmed into the memory 94 through a telemetry circuit 100 in telemetric communication with an external device 102, such as a programmer, transtelephonic transceiver, or a diagnostic system analyzer. The telemetry circuit 100 is activated by a control signal 106 from the microcontroller 60. The telemetry circuit 100 also allows intracardiac electrograms, status information relating to the operation of the device 10 (as contained in the microcontroller 60 or memory 94) to be sent to the external device 102 through the established communication link 104.

The stimulation device 10 further includes a physiologic sensor 110. Such sensors are commonly called "rate-responsive" sensors. The physiological sensor 110 is used to detect and generate a raw signal representing the activity of the patient, to which the microcontroller 60 responds by adjusting the rate and AV Delay at which the atrial and ventricular pulse generators, 70 and 72, generate stimulation pulses. The type of sensor used is not critical to the present invention and is shown only for completeness.

The stimulation device additionally includes a battery 114 which provides operating power to all of the circuits show in FIG. 1. For the stimulation device 10, which employs shocking therapy, the battery must be capable of operating at low current drains for long periods of time and then be capable of providing high-current pulses (for capacitor charging) when the patient requires a shock pulse. The battery 114 must also have a predictable discharge characteristic so that elective replacement time can be detected. Accordingly, the device 10 may employ lithium/silver vanadium oxide batteries, as is common in many such device to date.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that an external programmer 102 is in place to receive or transmit data, including NIPS procedure initializing parameters to the microcontroller 60 through the telemetry circuits 100 or instructions to initiate or terminate a NIPS procedure.

As further shown in FIG. 1, the device includes an impedance measuring circuit 120 which is enabled by the microcontroller 60 by a control signal 122. The known uses for an impedance measuring circuit 120 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock threshold; detecting when the device has been implanted; measuring stroke volume; and detecting the opening of the valves, etc. The impedance measuring circuit 120 is advantageously coupled to the switch bank 74 so that any desired electrode (including the RV and SVC coil electrodes, 36 and 38) may be used. The impedance measuring circuit 120 is shown only for completeness.

An important function of the device 10 is to function as an implantable cardioverter/defibrillator (ICD) device. That is, it is capable of detecting the occurrence of an arrhythmia, and automatically applying an appropriate electrical shock therapy to the heart aimed at terminating the detected arrhythmia. To this end, the microcontroller 60 further controls a shocking circuit 130 by way of a control signal 132. The shocking circuit 130 generates shocking pulses of low (up to 0.5 Joules), moderate (0.5–10 Joules), or high energy (11 to 40 Joules), as controlled by the microcontroller 60. Such shocking pulses are applied to the patient's heart through at least two shocking electrodes, and as shown in this embodiment, using the RV and SVC coil electrodes, 36 and 38, respectively. In alternative embodiments, the housing 40 may act as an active electrode in combination with the RV electrode 36 alone, or as part of a split electrical vector using the SVC coil electrode 38 (i.e., using the RV electrode as common).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

While a two chamber implantable stimulation device has been shown and described, the system and method for inducing a tachyarrhythmia may also be embodied in a multi-chamber device. For a complete description of an implantable stimulation device capable of pacing and sensing in two to four chambers and/or providing, anti-tachycardia pacing and shock therapy, see U.S. application Ser. No. 09/930,725, entitled "Multi-site cardiac stimulation device for controlling Interchamber Delay" (Richard Lu), filed Aug. 14, 2001, which application is incorporated herein by reference.

After either activity block 158 or activity block 162 is completed, the microcontroller determines if a condition exists to terminate the NIPS procedure. The first such condition is illustrated by decision block 164 wherein the microcontroller determines if there has been a capture failure. More particularly, in accordance with this embodiment, such a capture failure is a condition wherein a predetermined number of consecutive stimulation pulses have failed to capture the heart. A predetermined number of successive stimulation pulses failing to capture the heart may be, for example, two consecutive pulses. As previously mentioned, capture is preferably verified after each stimulation pulse. If capture fails it is noted by the microcontroller. In decision block 164, the microcontroller performs an analysis of the notations. If the notations indicate that two consecutive stimulation pulses failed to capture the heart, the process immediately returns.

The second set 144 of pulses, commonly referred to as the extra pulses, includes pulse S2, pulse S3, and pulse S4. The number of extra pulses may also be a programmable parameter and vary from that described herein. Each of the S2, S3, and S4 pulses also preferably has a programmable amplitude and pulse width of, for example, 4.5 V and 0.5 milliseconds, respectively. The last S1 pulse and the extra pulses are separated in time by interpulse intervals S1-S2, S2-S3, and S3-S4 which are progressively decreasing. The extra pulse interpulse intervals may be initially set by the programmer 102 and may be 280 milliseconds, 260 milliseconds, and 240 milliseconds, respectively. The intended purpose of the extra pulses is to place the last extra pulse, pulse S4, in accordance with this embodiment, in an overdriven cardiac cycle of the heart where the stimulated heart tissue is only partially refractory for inducing the tachyarrhythmia.

To place the pulse S4 as described above, the microcontroller 60 in accordance with this preferred embodiment and the stored NIPS protocol, adjusts or varies the interpulse intervals S2-S3, and S3-S4 in a prescribed manner after each group 140 of pulses is delivered to the heart. After each adjustment of the interpulse intervals, the pulse train is reinitiated and delivered to the heart. The foregoing process continues until the tachyarrhythmia is induced.

Figure 3:
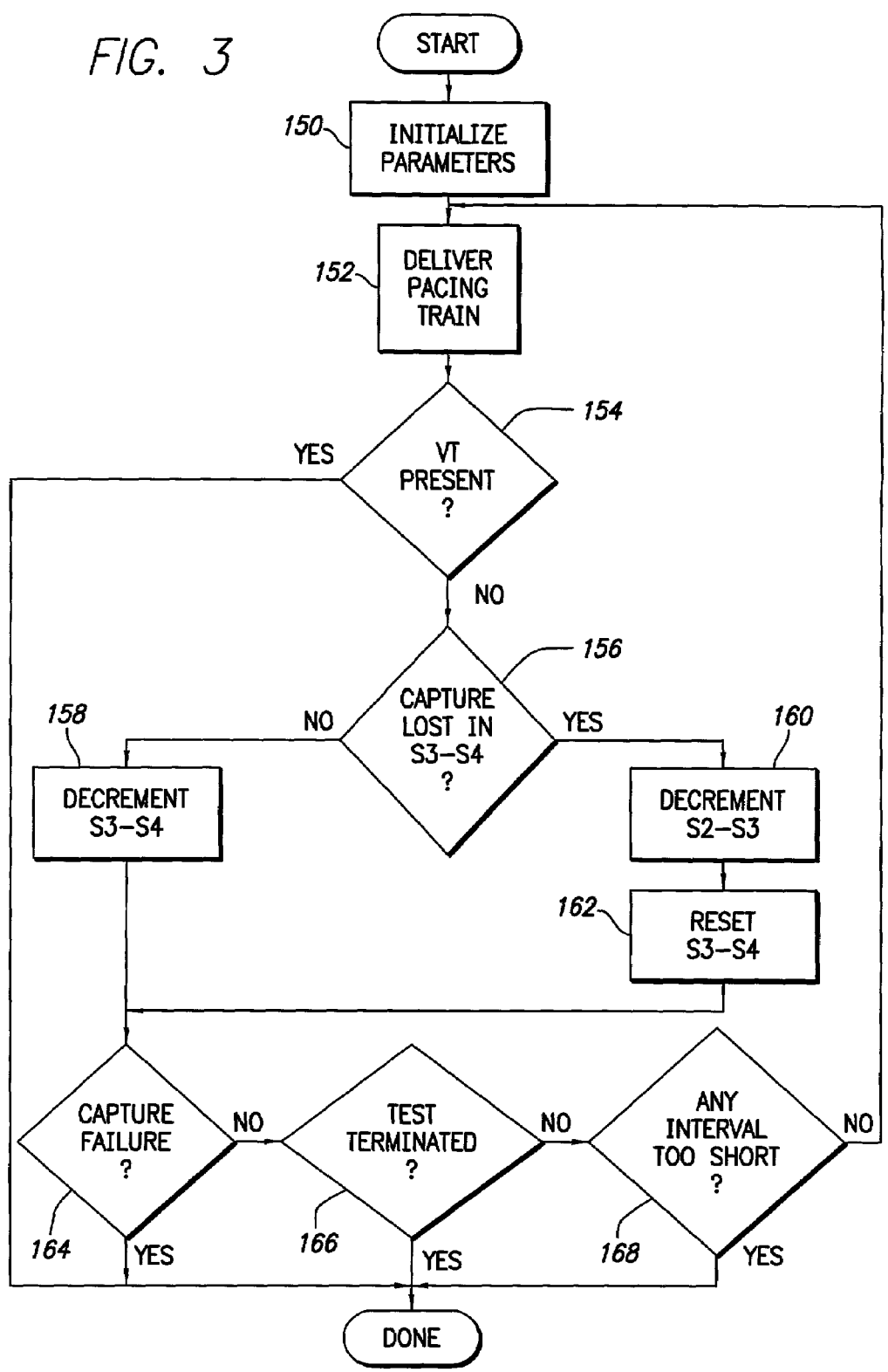
FIG. 3 shows a flow chart describing an overview of the operation of the device of FIG. 1 in accordance with the preferred embodiment of the present invention.

A prescribed manner in which the microcontroller 60 may vary the interpulse intervals and hence control the performance of the NIPS protocol of this embodiment is particularly illustrated in FIG. 3. In this flow chart, the various algorithmic steps are summarized in individual "blocks". Such blocks describe specific actions or decisions that are carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of FIG. 3 initiates at an activity step 150 wherein initializing parameters are provided to the microcontroller 60 or memory 94 via the telemetry circuit 100. It is, of course, assumed that the NIPS protocol to be implemented has already been stored in the memory 94 in the same manner. The initializing parameters may be, for example, the initial, or starting, values for S1-S1, S1-S2, S2-S3, and S3-S4 intervals, the amplitude and durations of the stimulation pulses, the time between successive pulse trains, and the interval by which each coupling interval will be adjusted as called for by the protocol. In alternative embodiments, shown in FIG. 4, the starting value for the inducing pulses may be a programmable value or a last successful value, and the adjustment may take the form of decrementing, incrementing, or "scanning", for example, in a binary fashion by alternately decrementing and incrementing, or equivalent, as will be described in more detail below. Also, at this time, any normal automatic capture back-up pulse function is suspended while capture verification is enabled on a beat-to-beat basis.

Figure 2:
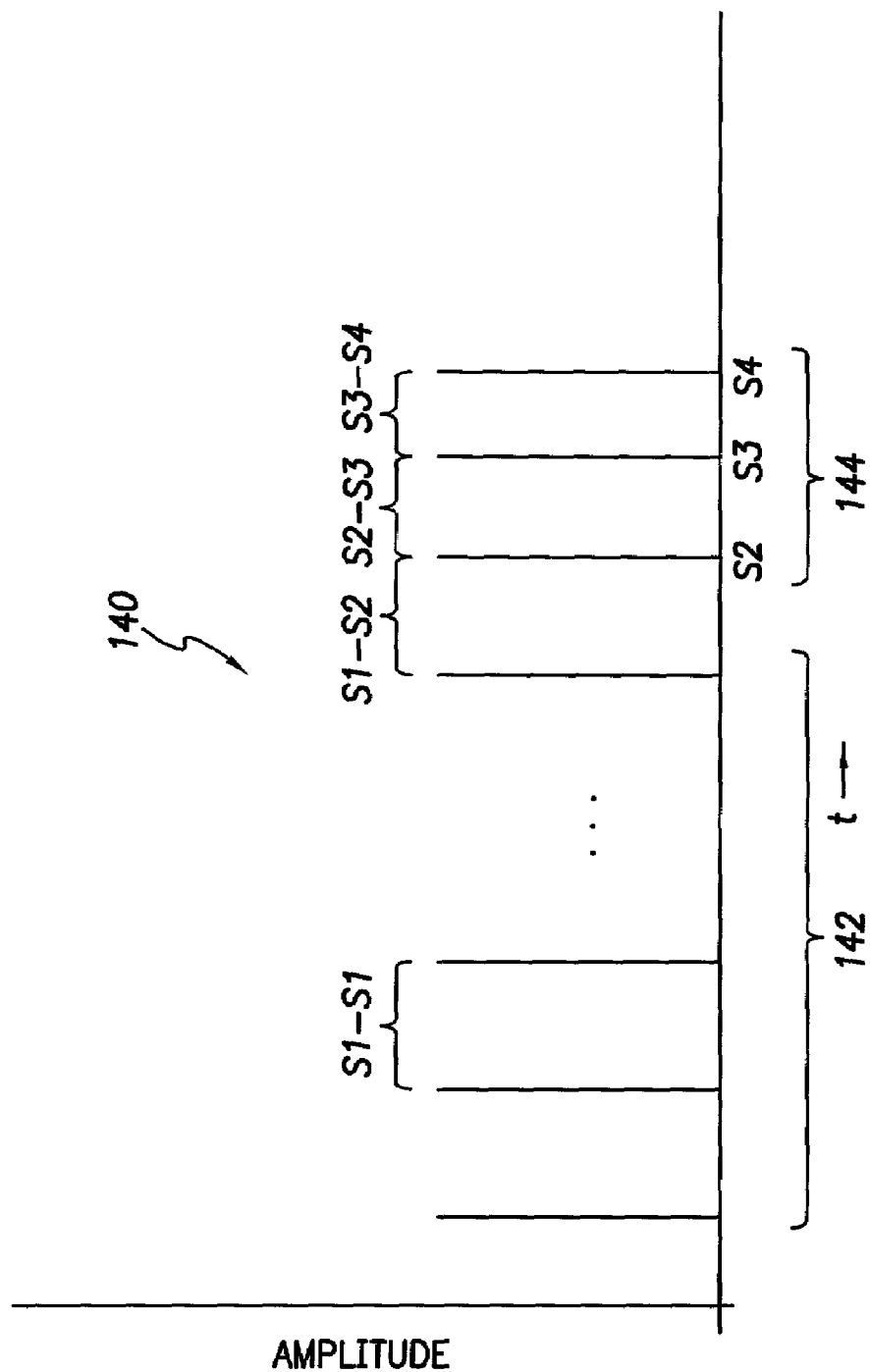
FIG. 2 shows one group of stimulation pulses which may be used for performing a NIPS procedure in accordance with the preferred embodiment of the present invention.

As shown in FIG. 3, after the initial parameters have been established, the process proceeds to activity step 152 wherein the microcontroller 60 causes the pulse generator 72 to deliver the first pulse train or first group of stimulation pulses as illustrated in FIG. 2 to the heart. After the first pulse train has been applied, the microcontroller next, in decision block 154 determines if the tachyarrhythmia has been induced. If the tachyarrhythmia is detected by the microcontroller, the process returns. However, if not, the process then advances to decision block 156. In decision block 156, the microcontroller determines if pulse S4 captured the heart. If pulse S4 captured the heart, the processor advances to activity step 158 to decrement the S3-S4 interpulse interval, by, for example, 10 milliseconds. If pulse S4 failed to capture the heart as determined in decision block 156, the process advances to activity blocks 160 and 162 in that order to decrement the S2-S3 interpulse interval and to reset the S3-S4 interval, if previously decremented, to its initial value. The process is now ready to reinitiate another pulse train with the adjusted intervals unless a termination condition exists to be described subsequently. Absence such a condition, the process will continue to adjust the interpulse intervals as described above after each pulse train. The pulse trains are reinitiated by the microcontroller until the tachyarrhythmia is detected in decision block 154.

After either activity block 158 are activity block 162 is completed, the microcontroller determines if a condition exists to terminate the NIPS procedure. The first such condition is illustrated by decision block 164 wherein the microcontroller determines if there has been a capture failure. More particularly, in accordance with this embodiment, such a capture failure is a condition wherein a predetermined number of consecutive stimulation pulses have failed to capture the heart. A predetermined number of successive stimulation pulses failing to capture the heart may be, for example, two consecutive pulses. As previously mentioned, capture is preferably verified after each stimulation pulse. If capture fails it is noted by the microcontroller. In decision block 164, the microcontroller performs an analysis of the notations. If the notations indicate that two consecutive stimulation pulses failed to capture the heart, the process immediately returns.

The next termination condition is illustrated by decision block 166. Here, the microcontroller determines if the NIPS procedure has been manually terminated by the clinician initiating a command to terminate the procedure from the external programmer 102. Such a command is received through the telemetry circuit 100 of the device 10. If a termination command is given, it will be noted by the microcontroller upon receipt and will be acted upon when the process reaches decision block 166. If such a notation of termination is present when the process reaches decision block 166, the microcontroller will terminate the NIPS procedure by immediately returning.

Lastly, the final termination condition is illustrated by decision block 168. Here, the microcontroller determines if any one of the interpulse intervals has been decremented to such as extent as to be shorter than the minimum interval required to support a beat-by-beat capture determination. If an interpulse interval is too short, the process immediately returns. If no pulse intervals is too short, the process reverts to activity block 152 to initiate the delivery of the next pulse train.

In FIG. 4, a more generalized embodiment is shown that includes several features for enhanced flexibility. In one embodiment, for example, the process may utilize any starting value (e.g., a maximum value, a minimum value, a programmable value, or a last successful value stored in memory) for the interpulse interval for the inducing pulses (e.g., S2, S3, S4, etc.). In another embodiment, the process may be adjusted in any direction (e.g., by decrementing, incrementing or any combination thereof) and will likely be selected based on the starting interpulse interval value. In another embodiment, the pulse train overdrive pulses, S1, may be varied after a predetermined time or number of attempts (e.g., from 400 ms to 375, from 375 ms to 350 ms, from 350 ms to 325 ms, or any predefined combination of programmable values, etc.). Furthermore, the generalized embodiment of FIG. 4 explicitly shows that the determination of the presence of a tachycardia (e.g., steps 253 and 262) may be either a ventricular tachycardia or an atrial tachycardia. These features have been combined into a single flow chart shown in FIG. 4 for convenience. It is recognized that one of skill in the art could readily eliminate, or make minor modifications to one or more of the features, or alter the order of the steps, and not depart from the spirit of the invention. What follows is a generalized description for all of these features.

The process begins at an activity step 250 wherein pacing parameters for S1, S2, S3, and S4 are initialized, including a starting interpulse interval for S2-S3 and S3-S4, which may be programmable values, e.g., a maximum value, a minimum value corresponding when the tissue is no longer refractory, or a last successful value that has been stored in memory. If the latter, then the microcontroller 60 and memory 94 have been programmed to store the last successful starting values from a previous attempt, and may even be further programmed to classify the last successful starting values according to the VT rate that was induced and the morphology of the rhythm. Once the pacing parameters are initialized, a first group of stimulating pulses, or pulse train, is delivered to patient's heart as illustrated in FIG. 2.

The process performs automatic capture detection at step 253 on a beat-by-beat basis for each of the pulses (e.g., S1, S2, S3, S4, etc). However, for simplicity of the flow diagram shown in FIG. 4, the step of determining capture is shown as a single step in dotted lines to indicate that it may be performed continuously and in the background. Any time that capture is lost, the process will terminate at step 280, and may also telemeter a message to the external programmer as to why the test has been terminated. The determination of capture eliminates the need for the physician to visually check for capture on an ECG strip, which can often be difficult to discern. For example, a loss of capture during the overdrive pulses, S1, indicates a failure to adequately entrain the heart. Entraining the heart ensures a regular rhythm, and thus a reasonably consistent refractory period, which helps in obtaining repeatable results. A loss of capture in any of the inducing pulses (e.g., S2, S3, S4, etc.) generally would indicate that the interpulse intervals of the inducing pulses are too short and falling in the refractory period.

In steps 254 and 262, the generalized flow chart of FIG. 4 explicitly indicates that the tachyarrhythmia determination may be a ventricular tachycardia determination (VT) or an atrial tachycardia (AT) determination. When ventricular tachycardia induction is performed, the process utilizes ventricular capture techniques, as described above. When atrial tachycardia induction is performed, the process utilizes atrial capture techniques.

Historically, atrial capture has been challenging due to the small signal size of the depolarization signal when compared to the large polarization signals and other noise. While conventional techniques that are employed in ventricular capture detection schemes may be used with low polarization leads for atrial capture, several alternate techniques have also been developed in recent years to detect atrial capture.

For example, in U.S. Pat. No. 5,601,615, Markowitz, et al. teaches that atrial loss of capture (ALOC) in response to an A-pace test stimulus is declared by the absence of a detected ventricular depolarization (V-event) in the latter portion of the paced A-V delay interval following the delivery of the A-pace test stimulus.

In U.S. Pat. No. 5,713,933, Condie, et al. utilize circuitry that monitors the cardiac impedance waveform during a predetermined capture detect window following delivery of stimulating pulses.

In U.S. Pat. No. 6,216,037, Van Oort discloses that "when the pacemaker sees a change in QT within the 2–10 ms range, this indicates failure of (atrial) capture, and responsive action is taken by either directly incrementing the energy level of the atrial pace pulses, or performing an atrial threshold search and then resetting the atrial pace energy level".

In U.S. Pat. No. 6,295,471, Bornzin et al. performs the test when the patient is at or near rest and monitors the patient's P-wave activity to determine a detection window where a next P-wave is expected to occur. The stimulation device then delivers an atrial pulse prior to the next detection window, and monitors the window to determine whether a P-wave occurs therein. If a P-wave does not occur, then atrial capture is present, while occurrence of a P-wave indicates absence of atrial capture. If atrial capture is absent, the stimulation device automatically determines an appropriate atrial pacing threshold by monitoring the detection window while adjusting the stimulation pulse energy level. The '471 patent further employs a "bottom-up" adjusting scheme which starts at a low energy level, below the expected atrial pacing threshold, and increases the energy level until atrial capture is detected, thus saving energy and further avoiding corruption by large polarization signals.

The '615, '933, '037, and '471 patents are hereby incorporated herein by reference, however, the type of capture detection system used is not critical in the implementation of the present invention.

Thus, once the pacing train has been delivered at 252, and capture has been verified in the appropriate chamber (i.e., ventricle or atrium), the process determines if a tachycardia (i.e., VT or AT) is present at step 254. If Yes, then the process terminates at step 280 and the device telemeters that induction has been successful. If no at step 254, then the interpulse intervals will be automatically adjusted as the defined by the protocol in steps 260–270. The protocol can be varied initially by preprogramming desired starting interpulse values for the inducing pulses and a direction of the adjustment.

For example, in the embodiment in FIG. 3, the starting interpulse values for inducing pulses are set to a maximum value and the interpulse intervals are decremented until capture is lost, thereby indicating that the interpulse interval is at a minimum value and the last stimulus fell into refractory tissue.

In another embodiment, the starting value for S3-S4 may be set to a minimum value (e.g., at or near the end of the refractory period, as determined either by testing for a loss of capture, or by programming an approximate value) and then incrementing the interpulse interval until a maximum value, or limit, is reached.

In yet another embodiment, a "last successful" value may be employed. That is, at implant, a starting value is selected by the physician, based on his own prior knowledge of this patient or a large population of patients in general (i.e., a best guess). Then, once electrophysiological testing has begun, the device can keep track of the pacing intervals that were successful in inducing VT, and repeat subsequent tests to determine repeatability with the last successful value. Accordingly, once a starting interpulse value has been selected, the adjustment may take the form of decrementing, incrementing, or "alternately scanning" by alternately decrementing and incrementing, for example, in a binary fashion or equivalent.

With this background, the automatic adjustment of the interpulse intervals, as defined by the protocol in steps 260–270 of FIG. 4, may now be described.

If the tachyarrhythmia is not detected by the microcontroller in step 254, the process then advances to step 260 to adjust the S3-S4 interpulse interval in a first direction (i.e., either by decrementing or incrementing one step, depending on the starting value and the desired protocol) and a subsequent pacing train is delivered. The step of capture verification (not shown) is again performed on a beat-by-beat basis in the background, and the process proceeds to the next step whenever capture exists.

If the tachyarrhythmia is not detected in step 262, then the process then advances to step 264 to adjust the S3-S4 interpulse interval in a second direction (i.e., again by either decrementing or incrementing, depending on the starting value and the desired protocol) and a subsequent pacing train is again delivered. In some instances the desired protocol may define the first and second directions to be the same direction, or, in another embodiment, in opposite or alternating directions.

The process will repeat at step 266 until a limit is reached for S3–S4, at which time the process determines at step 268 whether a limit has been reached for the adjustment of S2-S3 interval. If the limit has not been reached, then the S3-S4 interpulse interval is reset and the S2-S3 interpulse interval may be adjusted, and the process repeats by returning ultimately to step 252. The limits may be determined by a loss of capture, thereby indicating that the stimulation pulse is falling in refractory tissue. Alternatively, the limits may be programmed in at the time of induction testing or may be based on a number of unsuccessful attempts.

In yet another embodiment, the pacing train delivered in step 252 may also be varied. As such, an intermediate decision step is presented at step 284 to determine if the pulse train should be adjusted. The determination may be based on the total time elapsed without successful induction or a predetermined number of failed attempts. More specifically, if it is now time to adjust the pacing train, then the interpulse interval of the overdrive pulses within the pacing train may be automatically adjusted at step 286 (e.g., from 400 ms to 375, from 375 ms to 350 ms, from 350 ms to 325 ms, or any predefined combination of programmable values, etc.) before returning to step 252 wherein the protocol of varying the inducing pulses is repeated, as described above.

From the foregoing, it may be seen that the present invention provides a new and improved procedure for inducing a tachyarrhythmia of the heart to support an electrophysiological study. The improved procedure allows flexibility in the starting values and in the direction of the adjustments, while still providing complete automaticity once the induction protocol is underway. The procedure, such as a NIPS procedure, may be used to induce either a ventricular or atrial tachyarrhythmia. Since the procedure is truly automated, the tachyarrhythmia may be induced in less time, with less anxiety to the patient, and with reduced clinical cost.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. In an implantable cardiac stimulation device, a system that automatically induces a tachyarrhythmia of a patient's heart, the system comprising:
   a pulse generator that generates a series of pacing pulses separated in time by pacing intervals to a desired chamber of the patient's heart, the series having a predetermined number of overdrive pacing pulses followed by a predetermined number of inducing pacing pulses;
   a memory that stores starting values for the pacing intervals, and that further stores a predetermined direction for adjusting the starting values;
   a sensing system that senses when a tachyarrhythmia has been induced; and
   a control circuit, coupled to the pulse generator and the sensing system, that automatically adjusts the pacing intervals from the stored starting values in accordance with the predetermined direction when a tachyarrhythmia has not been induced, and then automatically triggers the pulse generator to deliver a subsequent series of pacing pulses using the adjusted pacing intervals.

2. The system of claim 1, wherein:
   the control circuit is configured to automatically terminate the delivery of the series of pacing pulses to the patient's heart when a tachyarrhythmia has been induced.

3. The system of claim 1, further comprising:
   a detector that detects the presence or absence of capture of the patient's heart by each delivered pacing pulse; and
   wherein the control circuit terminates the delivery of the pacing pulses to the patient's heart when capture is not detected in a predetermined number of pacing pulses.

4. The system of claim 1, wherein:
   the inducing pacing pulses comprises a last pulse ($S_N$) and a second-to-the-last pulse ($S_{N-1}$); and
   the control circuit adjusts the pacing interval between the second-to-the-last pulse and the last pulse ($S_{N-1}$ to $S_N$) in accordance with the predetermined direction until a predetermined limit is reached.

5. The system of claim 4, wherein:
   the inducing pacing pulses further comprises a third-to-the-last pulse ($S_{N-2}$); and
   the control circuit adjusts the pacing interval between the second-to-the-last pulse and the third-to-the-last pulse ($S_{N-2}$ to $S_{N-1}$) and resets the pacing interval between the second-to-the-last pulse and the last pulse ($S_{N-1}$ to $S_N$) to the starting value when the pacing interval between the second-to-the-last pulse and the last pulse ($S_{N-1}$ to $S_N$) reaches the predetermined limit.

6. The system of claim 4, wherein:
   the starting value is a minimum pacing interval that corresponds to non-refractory tissue; and
   the control circuit increases the pacing interval from the minimum starting value to a maximum finishing value.

7. The system of claim 4, wherein:
   the starting value is a predetermined maximum pacing interval; and
   the control circuit decreases the pacing interval from the maximum starting value to a minimum finishing value.

8. The system of claim 4, wherein:
   the starting value is a programmable pacing interval; and
   the control circuit sweeps the pacing interval through a range of intervals in at least one predetermined direction beginning with the programmed pacing interval.

9. The system of claim 4, wherein:
   the starting value is a last successful value that induced tachycardia; and
   the control circuit sweeps the pacing interval through a range of intervals about the last successful value using at least one predetermined direction.

10. The system of claim 1, wherein:
    the overdrive pacing pulses comprises a plurality of pulses ($S_1$) that are delivered at a pacing interval ($S_1$-$S_1$) that overdrives the patient's intrinsic rhythm; and
    the control circuit automatically adjusts the pacing interval ($S_1$-$S_1$) between the plurality of pulses ($S_1$) when either one of a predetermined number of unsuccessful attempts have been made or a predetermined time has elapsed.

11. The system of claim 1, wherein:
    the pulse generator generates the series of pacing pulses to the patient's atrium; and
    the control circuit automatically adjusts the pacing intervals when an atrial tachyarrhythmia has not been induced, and then automatically triggers the pulse generator to deliver a subsequent series of pacing pulses to the atrium using the adjusted pacing intervals.

12. The system of claim 1, further comprising:
    a telemetry circuit coupled to the control circuit; and
    an external device that communicates with the telemetry circuit and displays values for the pacing intervals after each adjustment by the control circuit.

13. In an implantable cardiac stimulation device, a system that automatically induces a tachyarrhythmia of a patient's heart, the system comprising:
    stimulation means for inducing a tachyarrhythmia in a desired chamber of a patient's heart using a series of pacing pulses separated in time by predetermined pacing intervals, the series having a predetermined number of overdrive pacing pulses followed by a predetermined number of inducing pacing pulses;

means for defining starting values for the pacing intervals and a direction for adjusting the starting values;

determining means for determining when a tachyarrhythmia has been induced;

adjusting means for automatically adjusting the pacing intervals between the inducing pacing pulses from the starting values in accordance with the defined direction when a tachyarrhythmia has not been induced; and control means for automatically triggering the stimulation means to deliver a subsequent series of pacing pulses using the adjusted pacing intervals when a tachyarrhythmia has not been induced.

14. The system of claim 13, wherein:

the control means further comprises means for terminating the delivery of the series of pacing pulses to the patient's heart when a tachyarrhythmia has been induced.

15. The system of claim 13, further comprising:

capture determining means that determines one of capture and loss of capture of the patient's heart in response to each delivered pacing pulse; and wherein the control means further comprises means for terminating the delivery of the series of pacing pulses upon loss of capture.

16. The system of claim 13, wherein:

the inducing pacing pulses comprises a last pulse ($S_N$) and a second-to-the-last pulse ($S_{N-1}$); and the adjusting means adjusts the second-to-the-last pulse and the last pulse ($S_{N-1}$ to $S_N$) pacing interval in accordance with the defined direction until a predetermined limit it reached.

17. The system of claim 16, wherein:

the inducing pacing pulses further comprising a third-to-the-last pulse ($S_{N-2}$); and the adjusting means adjusts the pacing interval between the second-to-the-last pulse and the third-to-the-last ($S_{N-2}$ to $S_{N-1}$) pulse interval and resets the second-to-the-last pulse and the last pulse ($S_{N-1}$ to $S_N$) pacing interval to the respective starting value when the ($S_{N-1}$ to $S_N$) pacing interval reaches the predetermined limit.

18. The system of claim 13, wherein:

the starting value for the pacing intervals is one of a maximum value, a minimum value that corresponds to non-refractory tissue, a programmable value, and a last successful value.

19. The system of claim 13, wherein:

the defined direction for adjusting the starting values of the pacing intervals is one of an increase, a decrease, or an alternating pattern of increasing and decreasing by at least one step.

20. The system of claim 13, wherein:

the stimulation means comprises means for inducing a tachyarrhythmia in the patient's atrium; and the adjusting means automatically adjusts the pacing intervals when an atrial tachyarrhythmia has not been induced, and then automatically triggers the pulse generator to deliver a subsequent series of pacing pulses to the atrium using the adjusted pacing intervals.

21. The system of claim 13, further comprising:

means for displaying the pacing intervals; and telemetry means for transmitting the pacing intervals after each adjustment by the adjusting means to the display means.

22. In an implantable cardiac stimulation device, a method of inducing tachyarrhythmias in a patient's heart, the method comprising:

generating a series of stimulation pulses to the patient's heart, the series having at least one overdrive stimulation pulse followed by at least two inducing stimulation pulses, the stimulation pulses being separated in time by interpulse intervals;

defining an induction protocol for adjusting the interpulse intervals, the induction protocol comprising a starting value for the interpulse intervals and a direction for adjusting the starting value;

determining when a tachyarrhythmia has been induced;

automatically adjusting the interpulse intervals in accordance with the induction protocol whenever the applied series of stimulation pulses fails to induce the tachyarrhythmia; and automatically triggering a subsequent series of stimulation pulses using the adjusted interpulse intervals in response to the failure to induce the tachyarrhythmia.

23. The method of claim 22, further comprising:

terminating the generation of the series of stimulation pulses to the patient's heart in response to a determination that a tachyarrhythmia has been induced.

24. The method of claim 22, further comprising:

determining capture of the patient's heart by each applied stimulation pulse.

25. The method of claim 24, further comprising:

terminating the generation of the series of stimulation pulses to the patient's heart when a predetermined number of stimulation pulses fail to capture the patient's heart.

26. The method of claim 24, wherein:

the adjusting step comprises automatically adjusting the interpulse intervals of the inducing stimulation pulses of each series in accordance with the induction protocol.

27. The method of claim 26, wherein the inducing stimulation pulses comprises a last pulse ($S_N$) and a second-to-the-last pulse ($S_{N-1}$), wherein:

the adjusting step comprises adjusting the interpulse interval between the second-to-the-last pulse and the last pulse ($S_{N-1}$ to $S_N$) until a predetermined limit is reached.

28. The method of claim 27, wherein the inducing stimulation pulses comprises a last pulse ($S_N$), a second-to-the-last pulse ($S_{N-1}$), and a third-to-the-last pulse ($S_{N-2}$), wherein:

the adjusting step comprises adjusting the interpulse interval between the third-to-the-last pulse and the second-to-the-last pulse ($S_{N-2}$ to $S_{N-1}$), and adjusting the interpulse interval between the second-to-the-last pulse and the last pulse ($S_{N-1}$ to $S_N$) to the starting interval in response to the last pulse ($S_N$) failing to capture the patient's heart.

29. The method of claim 22, wherein:

the defining step comprises defining the starting value to one of a minimum value that corresponds to non-refractory tissue, a maximum value, a programmable value, and a last successful value.

30. The method of claim 22, wherein:

the defining step comprises defining the direction for adjusting the starting values of the pacing intervals to one of an increase, a decrease, or an alternating pattern of increasing and decreasing by at least one step.

31. The method of claim 22, wherein:

the defining step comprises defining an induction protocol for inducing a tachyarrhythmia in the patient's atrium.

32. The method of claim 22, further comprising:

transmitting current interpulse intervals when adjusted by the adjusting means; and displaying the current values for the interpulse intervals on an external device.

* * * * *